United States Patent [19]

Winter et al.

[11] 4,424,703
[45] Jan. 10, 1984

[54] DEVICE FOR MONITORING THE CONCENTRATION OF AN AIR-VAPOR MIXTURE

[75] Inventors: Hans Winter; Eduard Mair; Holger Schoenewolf, all of Munich, Fed. Rep. of Germany

[73] Assignee: Siemens Aktiengesellschaft, Berlin & Munich, Fed. Rep. of Germany

[21] Appl. No.: 360,434

[22] Filed: Mar. 22, 1982

[30] Foreign Application Priority Data

Mar. 26, 1981 [DE] Fed. Rep. of Germany ....... 3112002

[51] Int. Cl.³ ............................................ G01N 29/02
[52] U.S. Cl. ........................................ 73/24; 118/712; 137/93; 364/497
[58] Field of Search ......................... 73/24, 290 V, 597; 364/497; 355/3 FU, 14 R, 14 FU; 118/689, 690, 712; 137/93; 222/DIG. 1

[56] References Cited

U.S. PATENT DOCUMENTS 3,834,806 9/1974 Whited ............................. 73/290 V
4,313,343 2/1982 Kobayashi et al. .............. 73/290 V
4,314,242 2/1982 Kuru et al. ....................... 73/290 V Primary Examiner—Stephen A. Kreitman
Attorney, Agent, or Firm—Hill, Van Santen, Steadman & Simpson

[57] ABSTRACT

A device for monitoring the concentration of an air-vapor mixture in the fixing station of a non-mechanical printing or copying device has an ultrasonic transducer for generating and receiving an ultrasonic signal in the fixing station, the transit time of the ultrasonic signal between transmission and reception indicating the air-vapor mixture concentration in the station. The transit times are subdivided into at least three ranges of which the mean range or mean ranges identify a desired concentration. An evaluator circuit post-connected to the ultrasonic transducer forms signals corresponding to the ranges, the signals being entered in one of at least three status memories in accordance with their significance. The status memory which is filled first emits an output signal for triggering a corresponding reaction such as increasing the vapor density in the station, and cancels the contents of all of the status memories. False reactions as a result of brief and topically limited fluctuations from a mean concentration are thus largely avoided.

7 Claims, 7 Drawing Figures

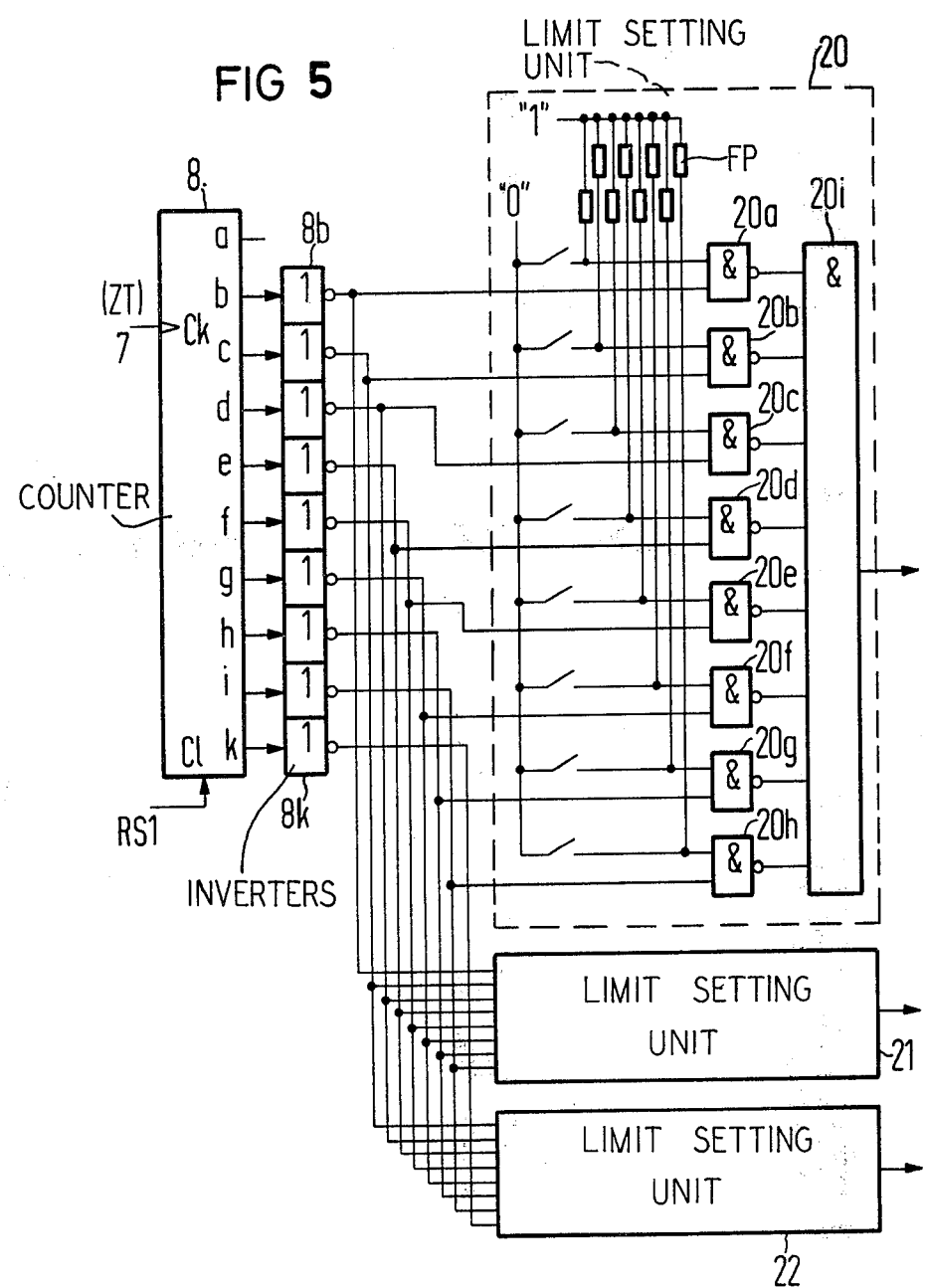

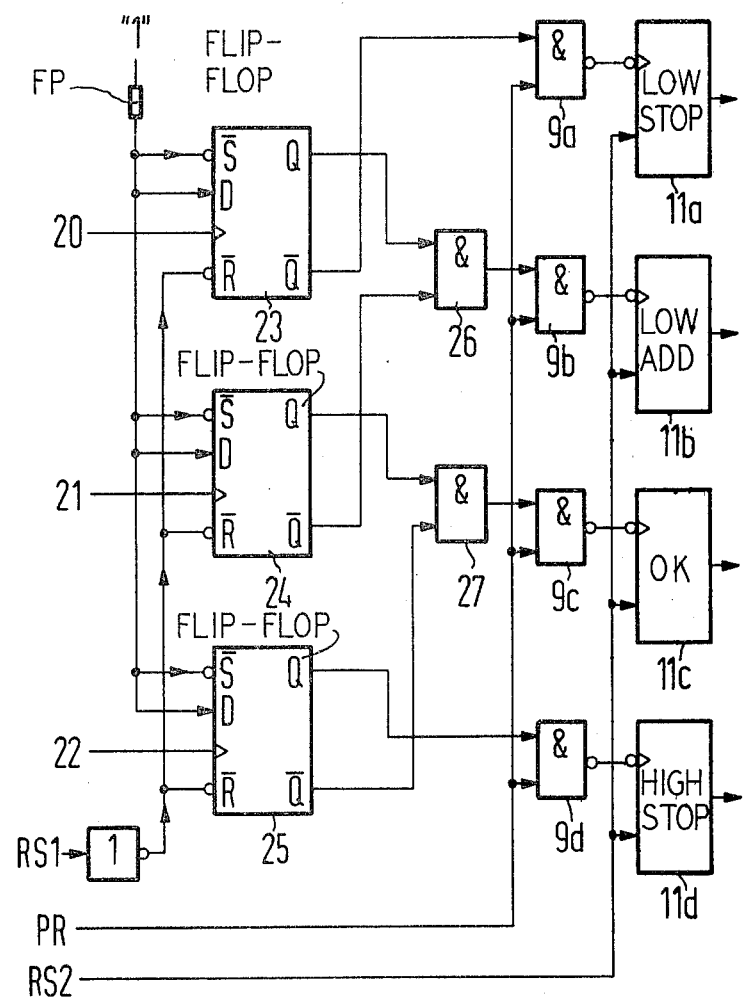

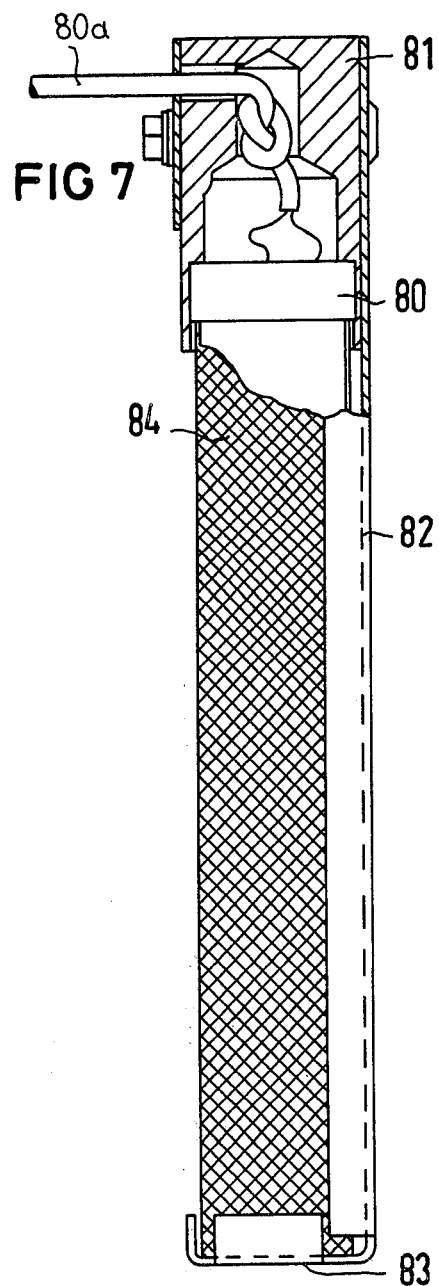

DEVICE FOR MONITORING THE CONCENTRATION OF AN AIR-VAPOR MIXTURE

BACKGROUND OF THE INVENTION

1. Field of the Invention

The present invention relates to devices for monitoring the concentration of an air/vapor mixture, and particularly for monitoring the concentration of solvent vapor in the fixing station of a non-mechanical printing or copying device.

2. Related Application

This application is related to the application of Holger Schoenewolf entitled Device for Monitoring the Concentration of an Air-Vapor Mixture, filed simultaneously herewith and identified with Ser. No. 360,433.

3. Description of the Prior Art

The use of solvent vapor to fix the toner images applied to a moving paper web in a fixing station of a non-mechanical printing or copying device is known from U.S. Pat. No. 3,049,810. The vapor, which may consist of Freon or methylene chloride, dissolves the toner so that it can penetrate into the paper. The fixing station in which the process takes place may consist, for example, of a container or housing including an evaporation location by means of which the solvent is converted from a liquid into a vapor. The paper web is conducted through the housing and is exposed to the solvent vapor inside the housing. A condensation trap is commonly attached in front of the container opening for preventing escape of solvent vapor into the environment.

A problem relating to the above known process and apparatus is that a perfect fixing of the toner images on the paper web can be achieved only when the solvent vapor has a specific concentration. It is therefore necessary that the concentration of the solvent vapor be determined within the fixing station by means of a measuring device and that the information obtained by the measuring device be employed to trigger an appropriate reaction if the concentration deviates from a desired level by an unacceptable amount.

Ultrasonic measuring devices operating on the principle that the transit time of an ultrasonic signal in a medium such as air varies depending upon the concentration of a vapor in the air are also known to those skilled in the art. One such ultrasonic measuring device is known, for example, from German AS 2,024,882 in which the electroacoustical transducer serves the function of transmitting the ultrasonic oscillation as well as receiving the oscillation which has been reflected by a reflector.

It is also possible to transmit a brief ultrasonic oscillation and to measure the time between the transmission of the pulse and the arrival of the reflected received pulse by the echo sounding principle. A means is then required to generate and count small time intervals between transmission and reception of the pulse in order to determine the transit time. An electronic clock may be employed for generating a number of clock pulses at equal intervals which are counted by the use of, for example, a binary counter.

Ideally a device disposed in the fixing station of a printing or copying machine for providing an electronic signal corresponding to the concentration of the solvent vapor therein should provide a signal to an evaluation logic means connected to the sensing device for determining whether the vapor concentration is within the specified range for proper operation, whether new solvent must be supplied and evaporated, or whether deviations from the specified value are so large that the printing or copying machine must be shut off.

A problem which is associated with any vapor concentration monitoring means which is used to control the operation of a device is that temporary disruptions in the vapor concentration may occur within the volume of air monitored by the sensor which may result in a changing of the density of the fixing agent vapor which is temporally and/or topically limited and therefore is not representative of the average density of the solvent vapor in the entire volume of the fixing station. Such disruptions may be caused by, for example, the formation of eddys due to spontaneous evaporation when the solvent is injected into the fixing station, thermal stratifications between the heated evaporation location and the condensation trap, and turbulences due to the moving paper web. These usually brief and spatially limited disruptions of the homogeneous distribution of the solvent vapor mixture have only a negligible influence on the fixing quality. The minimally different effect of the solvent in the vicinity of such temporary disruptions is balanced out over the longer fixing path.

Such disruptions do, however, significantly vitiate the measurements of the vapor concentration and the evaluation thereof in the limited volume of conventional detection devices. Diffractions of the ultrasonic wave may be caused which result in interference patterns, particularly due to the topical fluctuations of the vapor concentration. Such interference patterns may partially or entirely cancel the echo from the ultrasonic reflector or prevent the generation of useable electrical pulses at the receiver due to out-of-phase excitation of various portions of the sound-absorbing surface of the ultrasonic transducer.

SUMMARY OF THE INVENTION

It is an object of the present invention to provide a device for monitoring the vapor concentration of an air-vapor mixture, such as the solvent concentration in the fixing station of a non-mechanical printer or copier, which generates electronic signals corresponding to various concentration ranges and in which the probability for the initiation of false reactions as a result of temporally and locally limited concentration disruptions is significantly reduced.

The above object is inventively achieved in a vapor concentration monitoring device which has an electroacoustical transducer for generating an ultrasonic pulse and for converting a reflected ultrasonic signal into an electrical pulse after the ultrasonic pulse has traversed a volume of vapor, and which employs a binary counter for counting high frequency clock pulses durng the transit time with the outputs of the counting stages of the binary counter being supplied to a logic circuit for deriving a transmit pulse having a period equal to a selected plurality of periods of the ultrasonic pulse and for deriving a control signal for controlling a gate circuit for the received pulse. A read only memory is also employed which has address inputs connected to the outputs of selected counting stages of the binary counter, the addresses of the read only memory which are called during the evaluation time are classified in at least three ranges with continuous addresses, the information output from the read only memory being identical within the ranges, but different outside of the ranges. A register for transfer of the information from the outputs of the read only memory is triggered by the received pulse for initiating an appropriate reaction in accordance with the monitored vapor concentration.

The receive pulse may be synchronized with the counting clock such that the transfer of the information from the outputs of the read only memory to the register is undertaken in synchronization with the counting clock.

BRIEF DESCRIPTION OF THE DRAWINGS

FIGS. 5 and 6 are block diagrams of a further embodiment for the selector shown in FIG. 1.

FIG. 7 is a side view, partially broken away, of a test probe for use in the fixing station of a non-mechanical printer or copier in combination with the evaluation circuitry shown in FIGS. 1 through 6.

DESCRIPTION OF THE PREFERRED EMBODIMENTS

Figure 1:
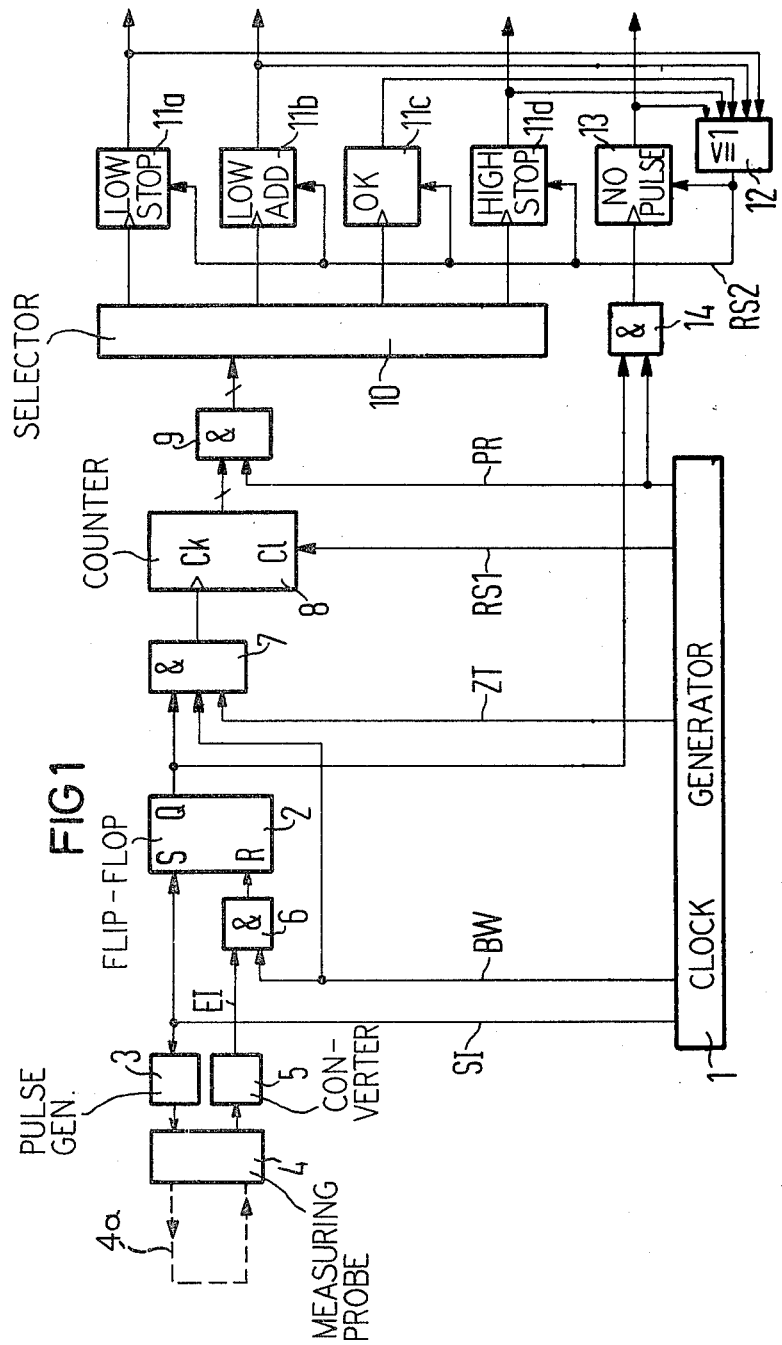
FIG. 1 is a block diagram for a device constructed in accordance with the principles of the present invention for monitoring the concentration of an air-vapor mixture.

A device for monitoring the concentration of an air-vapor mixture such as the concentration of solvent vapor in the fixing station of a non-mechanical printing or copying device is shown in FIG. 1. The device includes a clock generator 1 which has an oscillator for generating a high frequency counting clock pulse sequence, a binary counter, and a logic combinatorial circuit for deriving control signals. The detailed manner of operation of the clock generator 1 and the individual components therein are described below in connection with FIGS. 2 and 3. The counting clock pulses are supplied preferably by a quartz-stabilized quartz oscillator with a period of, for example, a few microseconds. The clock pulses continuously increment the binary counter until attainment of a maximum counter reading of 1 . . . 11, so that the next input pulse generates a counter reading of 0 . . . 00. This change or the next change defines the beginning of a transmit pulse SI which lasts approximately 128 microseconds. The transmit pulse SI sets a flip-flop 2 and gates an oscillation pulse with an ultrasonic frequency of, for example, 200 kHz generated by a pulse generator 3. The electrical oscillation is converted to an acoustical wave by means of an ultrasonic transducer in a measuring probe 4. The acoustical signal traverses a measuring path 4a in the volume of vapor which is being monitored and is reflected at the end of the path and arrives back at the ultrasonic transducer after a transit time which is dependent on the solvent vapor concentration. After reconversion into an electrical signal, a converter circuit 5 forms a digital receive pulse EI from the reconverted signal which again resets the flip-flop 2. This, however, is only possible when the received pulse EI is generated in an evaluation time span which may begin, for example, 1024 microseconds after the beginning of the transmit pulse SI and ends after a further 1024 microseconds. The evaluation time span is defined by a signal BW emitted by the clock generator 1. The signal BW controls a gate circuit 6, which may be an AND gate, which either transmits or blocks the receive pulse EI depending upon its chronological position.

The clock generator 1 also generates a series of counting clock pulses on a line ZT which may have respective durations of, for example, two microseconds. The counting clock pulses ZT are supplied to an AND gate 7 having the output Q of the flip-flop 2 and the signal BW as its other inputs. When the AND gate 7 is enabled by coinciding signals at the inputs connected to the flip-flop output Q and the signal BW, the counting clock pulses ZT are transmitted through the AND gate 7 to a binary counter 8. The control of the counting clock ZT by the signal BW through the AND 7 may be omitted, however, the required counting capacity of the binary counter 8 must then be enlarged. If such control is omitted, a doubling of the counting capacity of the counter 8 would be required if the aforementioned values for the beginning and end of the evaluation time span are used.

The counter reading of the binary counter 8 upon the arrival of a receive pulse EI is a measure of the acoustical transit time for the ultrasonic signal in the measuring probe 4, and is thus also a measure of the solvent vapor concentration at that moment. The counter reading corresponds to the overall transit time when the through-connection of the counting clock ZT is controlled only by the flip-flop 2. If the additional control by means of the signal BW is used, the time from the beginning of the transmit pulse SI until the beginning of the evaluation time span must also be added to the time determined from the counter reading. This does not play a fundamental role in determining the vapor concentration, however, because the second time span is constant and need only be matched in accordance with the significance assigned to the individual counter readings.

A further control gate 9, which may be an AND gate is connected to the outputs of the binary counter 8. The control gate 9 has a plurality of inputs corresponding to the number of output stages of the binary counter 8 and an additional input connected to the clock generator 1 for receiving a transfer signal PR. Upon the occurrence of the transfer signal PR, the gate 9 transfers the information pending at the counter output to a selector 10. The binary counter 8 is then reset by means of a pulse RS1 from the clock generator 1 which occurs before the emission of the next transmit pulse SI.

The selector 10, which is described in detail below, performs the function of classifying the possible counter readings from the binary counter 8 within the evaluation time span into three or four ranges and, in accord with the final counter reading, selecting one of three or four status memories. The sample embodiment shown in FIG. 1 employs four status memories 11a, 11b, 11c and 11d which have specific, preferably identical, memory capacities. Upon each selection of a status memory, its remaining capacity is reduced by one bit. That status memory whose capacity is first exhausted emits an output signal which, via an OR gate 12, generates a signal RS2 for resetting all of the status memories 11a through 11d and, under certain conditions, produces a predetermined reaction to insure that the solvent vapor concentration remains in or returns to a desired range. The status memories 11a through 11d preferably consist of multi-stage binary counters.

In the embodiment shown in FIG. 1, the following meanings are respectively associated with the status memories 11a through 11d which initiate reactions as follows. If the status memory 11a is first emptied, this indicates a solvent concentration which is unacceptably low and the printing or copying device is stopped. If the status memory 11b is first emptied, this indicates a solvent concentration which is too low, but correctable, and more solvent is added to the fixing station. If the status memory 11c is first emptied, this indicates acceptable concentration within a rated range, and no reaction is needed. Finally, if the status memory 11d is first emptied, this indicates a solvent concentration which is unacceptably high, and the printer or copier is stopped.

A further status memory 13 is selected via an AND gate 14 when no received pulse EI was registered during the evaluation time span and, accordingly, the flip-flop 2 is still set. An output signal from the status memory 13 resets all of the status memories 11a through 11d, as well as the memory 13, and causes the printer to stop. When the status memory 13 is the first memory at which an output signal occurs, one can assume with a high probability that a malfunction of the measuring probe exists.

The use of the status memories 11a through 11d and the status memory 13 prevents the triggering of reactions as a consequence of the results of individual measurements, that is, measurements which represent only a topically or temporally limited portion of the total volume of the fixing station. Such individual measurements are susceptible to the disruptive influences identified above, thereby resulting in false measurements which may initiate a reaction which is in fact not needed. The measuring results obtained with the device disclosed and claimed herein are supplied to the various status memories so that a particular condition within the fixing station must exist during the course of more than one measurement pulse emitted by the measuring probe 4 so that temporally limited disruptions have virtually no effect insofar as triggering an inappropriate reaction. When a vapor concentration in a range outside of the acceptable range does occur, however, the status memory associated with that particular concentration range will be emptied relatively quickly so that an appropriate reaction can be undertaken without undue delay. False measurements can be further prevented by a special embodiment of the measuring probe 4, described in greater detail below.

Figure 2:
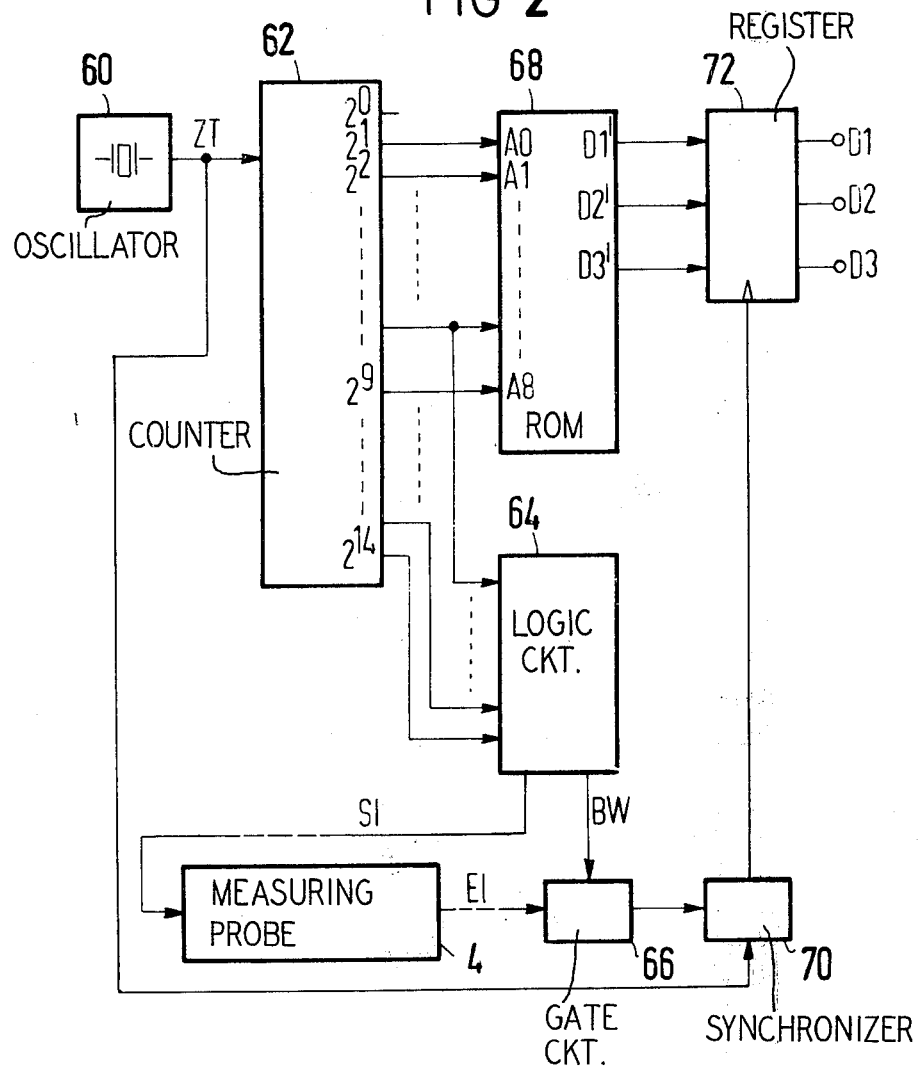
FIG. 2 is a block diagram of an exemplary embodiment of the clock generator and selector employed in FIG. 1.
Figure 4:
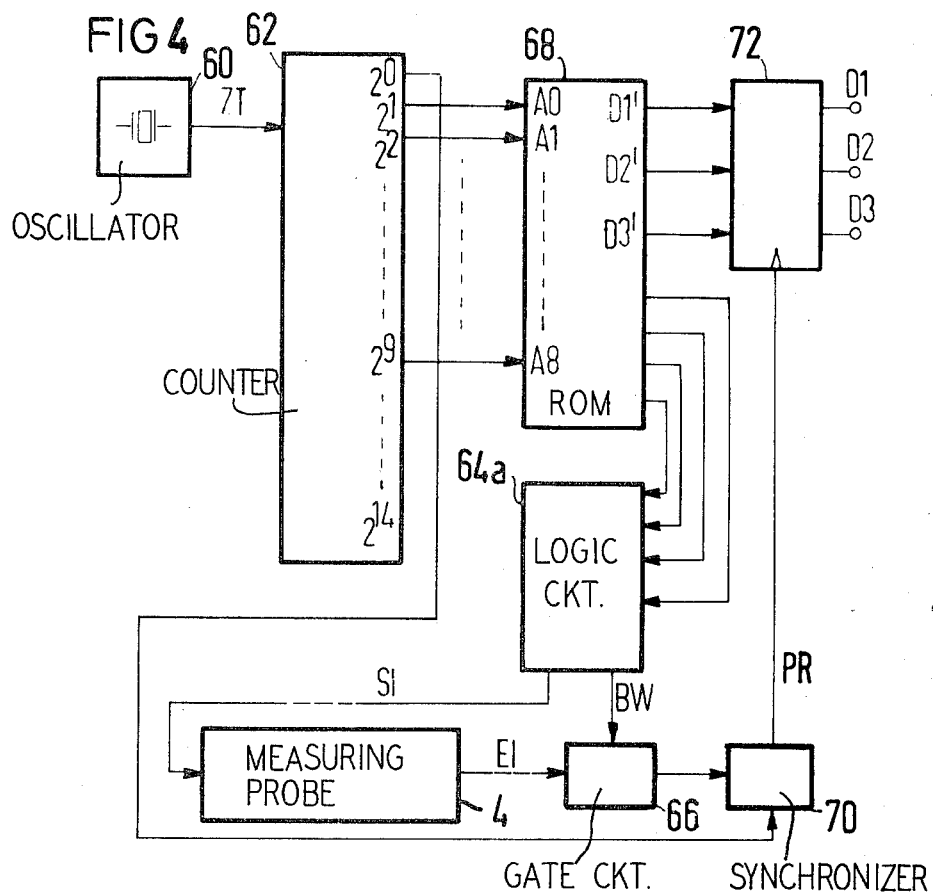
FIG. 4 is a block diagram for an embodiment of the clock generator and a second embodiment of the selector for use in the circuit of FIG. 1.

One embodiment for realizing the selector 10 is shown in FIGS. 2 and 4 wherein the selector is a programmable read only memory 68. The elements of the clock generator 1 previously described in connection with FIG. 1 are also shown in FIGS. 2 and 4 including an oscillator 60 for generating the counting clock pulses ZT with a period of, for example, one microsecond, and a binary counter 62 to which the clock pulses ZT are supplied. The binary counter 62 has 15 counting stages $2^0$ through $2^{14}$ and is operated without external resetting, so that a counter reading of 0 ... 00 follows a counter reading 1 ... 11. The change-over to the counter reading 0 ... 01 is defined as the first counting step. Thus, given the conditions for the sample embodiment described above, first counting steps have a chronological spacing of approximately 32 microseconds. The transmit pulses SI are also transmitted with this spacing.

The transmit pulses SI are generated by a portion of a logic combinatorial circuit 64 having inputs connected to selected ones of the outputs of the counting stages of the binary counter 62. The individual connections depend upon the desired duration of the transmit pulse SI, which is 128 microseconds in this embodiment.

A second portion of the logic combinatorial circuit 64 generates the control signal BW for controlling a gate circuit 66 for the receive pulse EI. The control signal BW is also generated by counter readings from selected ones of the outputs of the binary counter 62 which determine the time span during each complete counter cycle of the counter 62 during which receive pulses EI are evaluated. Receive pulses which may arrive outside of the evaluation time span or "measuring window" are not evaluated. Calculating from the beginning of the transmit pulse SI, the control pulse BW may begin, for example, after 1024 microseconds and end after 2048 microseconds.

Figure 3:
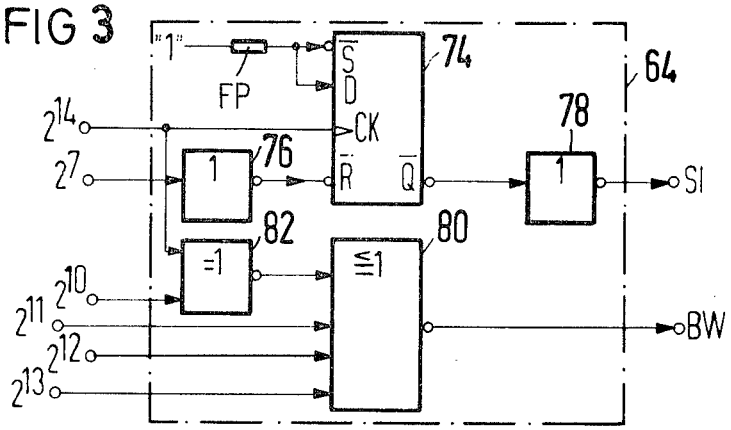
FIG. 3 is a block diagram of an exemplary embodiment of the logic circuit shown in FIG. 2.

One embodiment for the logic combinatorial circuit 64 for deriving the transmit pulse SI and the control signal BW is shown in FIG. 3. This circuit is designed with the assumption that inverted output signals from the counter stages of the binary counter 62 are not available. The sub-circuit for generating the transmit pulse SI essentially consists of a D flip-flop 74 having a clock input CK which is connected to the output of the counter stage $2^{14}$ of the binary counter 62. The set input $\overline{S}$ and the data input D are supplied with a fixed potential corresponding to a binary "1" via a resistor FP. The reset input $\overline{R}$ of the D flip-flop 74 is controlled by means of the output signal of the counting stage $2^7$ inverted by an inverter 76. The signal tapped at the output $\overline{Q}$ of the flip-flop 76 is amplified by means of an inverting driver stage 78 whose output is the transmit pulse SI.

The control signal BW is generated by a NOR gate 80 having inputs directly connected to the outputs of the counter stages $2^{11}$, $2^{12}$ and $2^{13}$ and an input connected to the outputs of the counter stages $2^{10}$ and $2^{14}$ via a NAND gate 82.

The outputs of the low significance counter stages of the binary counter 62 are connected to the address inputs of the read only memory 68, as shown in FIG. 2. The address input A0 is connected to the output of the counter stage $2^1$, the address input A1 is connected to the output of the counter stage $2^2$, etc. Thus, an address change occurs after every second pulse of the counting clock ZT. With the periods described above, measurement can be undertaken with a resolution of the two microseconds.

In the sample embodiment, the binary counter 62 is simultaneously employed as the clock pulse counter 8 as well as the binary counter for the clock generator 1 shown in FIG. 1. By so doing a simplification of the circuit is achieved.

Any commercially available module with a sufficient address capacity and with at least three parallel outputs may be employed as the read only memory 68. The content may be fixed or variable. Under certain conditions, the counting clock or the output pulses of the $2^0$ stage of the binary counter 62 may be used as a clock. In the sample embodiment, a module with a storage capacity of 512×8 bits is employed as the read only memory 68. The address capacity thus amounts to $2^9$ addresses. Becauasge a change of address occurs every two microseconds, the cell of all addresses lasts 1024 microseconds, which is precisely the time span between the beginning of the transmit pulse SI and the beginning of the evaluation time span, and is also the duration of the evaluation time span itself. This means that all memory addresses are completely run through for a second time during the evaluation time span. This, however, is not a necessary condition and the evaluation time may be shorter if desired.

Of the outputs of the read only memory 68 which are available, only the outputs D1', D2' and D3' are used. The memory content is such that the output D2' shows a logical "1" and the outputs D1' and D3' show a logical "0" for all addresses of an address range. In the lower address range the output D1' exhibits a logical "1" and the other outputs show a logical "0" and in the upper address range the output D3' shows a logical "1" and the other outputs exhibit a logical "0". This coding is an exemplary embodiment only and different coding may be employed for the three different statuses in a manner known to those skilled in the art.

Upon the beginning of the receive pulse EI (when the receive pulse EI falls within the evaluation time span) the information at the outputs D1' through D3' of the read only memory 68 are transferred into a register 72. Depending upon the technical execution of the read only memory 68 and the register 72, it may be preferable or necessary for reliable information transfer to synchronize the receive pulse EI with the counting clock ZT or with the output pulses of the $2^0$ stage of the binary counter 62. A synchronizing circuit 70 which may be, for example, a D flip-flop serves this purpose. The information characterizing the vapor concentration is then available at the outputs of the register 72 for one measuring cycle.

The position and size of the mean address range can be easily determined from a rated value and admissible tolerances of the vapor concentration for each specific use because the respective address of the read only memory 68 is a function of the time which has elapsed since the beginning of the transmit pulse SI, and the information transfer into the register 72 depends on the transit time of the ultrasonic signal, and thus, on the concentration of the air-vapor mixture to be monitored.

Instead of a subdivision of the memory addresses into three ranges more ranges such as, for example, five ranges may be selected. For example, transit times of the ultrasonic signal which coincide with the call of the addresses of the two extreme ranges may trigger an immediate shut down of the printing or copying device.

The employment of a read only memory for determining specific ranges of the transit time of the ultrasonic signals, and thus, of the concentration of the solvent vapor, has the advantage of simple adaptation to altered conditions by means of reprogramming the memory or interchanging memory modules.

With the above-indicated dimensioning for the circuit shown in FIG. 2, a comparatively long pause of approximately 30 milliseconds arises between the end of the measuring time span and the next transmit pulse SI. This time, however, is selected such that all ultrasonic signals which could arise due to reflections at housing walls of the fixing station and other objects in the fixing station, which would falsify the desired measured result, have sufficient time to decay.

In some cases it may not be necessary to count the trailers of the receive pulses due to existing environmental conditions so that the waiting time between the end of the evaluation time span and the generation of a new transmit pulse SI can be significantly abbreviated. In such cases, given a corresponding reduction of the counter capacity of the binary counter 62, the address capacity of the read only memory 68 can be made equal to the counting capacity. The beginning and end of a transmit pulse SI and of the evaluation time span can then be marked in a simple manner by means of read signals from the read only memory 68. A sample embodiment for such a circuit is shown in FIG. 4. The inputs of the logic combinatorial circuit 64a are connected to corresponding outputs of the read only memory 68. The logic combinatorial circuit 64a consists of two flip-flop circuits which are respectively set and reset by means of the read signals from the read only memory 68. If such clocked flip-flop circuits are used, the counting clock ZT must also be supplied to the combinatorial circuit 64a.

The length of the transmit pulse and the position and duration of the evaluation time span can also be changed by means of a change of the memory content.

A sample embodiment for the selector device 10 which is even more easily adaptable to altered conditions but which requires a greater outlay is schematically illustrated in FIGS. 5 and 6. The sample embodiment shown in those figures is based on time spans already described in the above example, particularly for the pulse spacing of the counting clock pulse ZT and for the duration of the evaluation time span. Further, it is assumed that the through-connection of the counting clock ZT to the input of the clock pulse counter 8, as shown in FIG. 1, occurs only during the evaluation time span.

In FIG. 5, the outputs of the counting stages of the clock pulse counter 8, which consists of a plurality of counter modules, are referenced with a through k, the output a being of the lowest significance and the output k being of the highest significance. A plurality of inverters 8b through 8k are respectively directly connected to the outputs b through k. The pulse input CK of the clock pulse counter 8 is connected to the output of the AND element 7 shown in FIG. 1. The control input C1 serves the purpose of resetting the counter 8 by the use of a reset pulse RS1.

As further shown in FIG. 5, three limit setting units 20, 21 and 22 are provided for setting the limits between the ranges for the counter readings or for the selection of the individual status memories. The limit setting units 20, 21 and 22 are identical, with the internal details being shown in FIG. 5 for limit setting unit 20 only. Each of the limit setting units, such as unit 20, contains the same number of NAND elements with two inputs each, each of the NAND elements having an output connected to a common multiple input AND gate, which has an output which serves as the output for the unit. Although there are nine inverters 8b through 8k, only 8 NAND elements 20a through 20h are utilized in the limit setting units, such as the unit 20, for determining the limit between the first and second region, with the consequence that this limit can lie only in the first half of the evaluation time span.

The first inputs of the NAND elements 20a through 20h are connected via resistors FP to a fixed potential corresponding to a bindary "1", however, the first inputs may also be connected to a logical "0" potential via a switch or a solder bridge. The second inputs of the NAND elements 20a through 20h are respectively connected to the outputs of the inverters 8b through 8k. All NAND elements whose first inputs are connected via closed switches or solder bridges to the "0" potential emit a binary "1" at their respective outputs independently of the respective logical statutes at the second inputs. The output signals of all other NAND elements correspond to the output signals of the associated counting stages. When these counting stages emit a binary "1", all NAND elements 20a through 20h now emit a binary "1" and the post-connected AND gate 20i with 8 inputs responds accordingly. Due to the rising edge of the output signal, a first D flip-flop, shown in FIG. 6, is set, whereby the output signal of the AND gate 21i effects the input of a binary "1" adjacent to the data input D as a fixed potential into the flip-flop 23. This means that the first range limit, that is, the limit between the first and second range, was reached by counter readings with the most recentle elapsed counter step.

In a corresponding manner, a second flip-flop 24 is set by an output signal from the limit setting unit 21 and a third flip-flop 25 is set by an output signal from the limit setting unit 22 when the associated range limits perscribed by the setting of the particular limit setting unit have in fact been reached.

The manner of setting the flip-flops 23, 24 and 25 described above presumes that when the third flip-flop 25 is set, the first flip-flop 23 and the second flip-flop 24 have already been set. The output signals from the first and second flip-flops 23 and 24 must therefore be inhibited so that the signal from the third flip-flop 25 is the controlling signal. This is undertaken by the use of two AND gates 26 and 27 which always prevent forwarding of the output Q of a flip-flop proceeding from that point in time at which the flip-flop of the next-highest range in set.

Therefore, the following conditions apply for selection of the status memories 11a through 11d:

Status memory 11a: flip-flop 23 not set;
Status memory 11b: flip-flop 23 set;
Status memory 11c: flip-flop 24 set;
Status memory 11d: flip-flop 25 set.

Because the setting of the flip-flops 23 through 25 can occur only upon discrete counter readings, and thus, only in chronological succession, the forwarding of the counting results to the selector 10 according to FIGS. 5 and 6 must occur constantly and cannot be postponed until after termination of the evaluation time span, as may occur in the simplified embodiment shown in FIG. 1 wherein the selector 10 is realized by a programmable read only memory. When the selector 10 is realized as shown in FIGS. 5 and 6, a limiting state governing the selection of a status memory exists only at the outputs of the flip-flops. A gate control arrangement consisting of NAND elements 9a, 9b, 9c and 9d, each controlled by a transfer signal PR is therefore provided between the outputs of the flip-flops 23 and 25 and the AND gates 26 and 27, which serve as the outputs for the selector 10, and the status memories 11a and 11d.

By the use of the above-described evaluating means, specific reactions such as increasing the supply of solvent for increasing the vapor concentration or shutting off the printing or copying device do not occur on the basis of an individual measurement but are instead made dependent upon the predominating result of a plurality of measurements. This greatly reduces the probability that the causes of such reactions are in fact only simulated by the types of disruptive influences within the fixing station described above, thereby triggering a false and unwanted reaction.

In order to further decrease the possibility of the initiation of false reactions, an ultrasonic measuring probe 4 which is in large part protected against such disruptive influences may be utilized. Such a probe is described in the copending application of Eduard Mair, filed simultaneously herewith and having Ser. No. 360,432, assigned to the assignee of the subject matter disclosed and claimed herein. Such a probe is shown in FIG. 7.

The probe shown in FIG. 7 has an ultrasonic transducer 80 seated in a housing 81 consisting of a dimensionally stable, oscillation-attenuating synthetic in such a manner that as little acoustical coupling as possible exists between the transducer 80 and the other elements of the probe fastened to the housing 81. The probe further consists of a U-shaped member 82 which is fastened to the housing 81 and is bent at right angles at its opposite end. The bent portion of the element 82 forms a reflector 83 at which the ultrasonic waves emitted by the ultrasonic transducer 80 are reflected and returned to the ultrasonic transducer 80. The distance between the ultrasonic transducer 80 and the reflector 83 may be, for example, 150 millimeters and defines the measuring path which is traversed twice by the ultrasonic signals during the transit time.

The entire measuring path is surrounded by a mesh tube 84 consisting of a fine-mesh net. In a preferred embodiment, the net consists of wires having a diameter of approximately 0.06 millimeters which are woven with one another such that an open screen surface of approximately 40% results. This value is a compromise in order to insure that the vapor concentration inside of the mesh tube 84 follows changes in the average vapor concentration outside of the mesh tube 84 with sufficient rapidity while the interior of the tube 84 is screened as well as possible from brief and topically limited concentration fluctuations. Inferference phenomena caused by diffraction of the sound field in the measuring path are substantially eliminated and the mesh tube 84 additionally suppresses false echo signals which may otherwise derive from the environment. The probe has an input/output line 80a which is connected to the pulse generator 3 and the converter 5 as shown in FIG. 1.

Although modifications and changes may be suggested by those skilled in the art it is the intention of the inventors to embody within the patent warranted hereon all changes and modifications as reasonably and properly come within the scope of their contribution to the art.

We claim as our invention:

1. A device for monitoring the concentration of an air-vapor mixture having a measuring probe inserted in a mixture to be monitored having an electroacoustical transducer for converting an electrical transmit pulse into ultrasonic signal pulses, a reflector for reflecting said ultrasonic signal pulses back to said transducer for reconversion of said ultrasonic signal pulses into an electrical receive pulse afer a transit time of said ultrasonic signal pulses in said mixture, said device having a circuit for evaluating said transit time and thereby determining the concentration of said mixture comprising:

a clock pulse generator for generating counting clock pulses and for periodically generating said transmit pulse;

a clock pulse counter for counting said clock pulses which elapse between the beginning of a transmit pulse and the beginning of a receive pulse;

at least three status memories having predetermined identical memory capacities;

a selector means interconnected between said transducer and said status memories for supplying a signal to one of said status memories which reduces the remaining capacity of the selected status memory by one unit, said selector means supplying said signals to respective status memories as a function of the transit time of said ultrasonic signal pulses in said mixture, whereby a status memory having a capacity which is first exhausted supplies a control signal for initiating a predetermined reaction for maintaining said concentration within a predetermined range.

2. The device of claim 1 further comprising an additional status memory which is selected by said selector means when no receive pulse has been generated by said transducer within a preselected evaluation time span following a beginning of said transmit pulse.

3. The device of claim 2 wherein said additional status memory is a counter.

4. The device of claim 1 wherein said status memories are counters.

5. The device of claim 1 wherein said selector means comprises:

at least two limit setting units for adjustably defining the limits between the ranges of counter readings of said binary counter which respectively cause a signal to be supplied to one of said status memories, each limit setting unit including a coincidence circuit connected to said binary counter for generating an output signal upon coincidence of all output signals of said binary counter in accordance with the limit for the respective limit setting unit;

at least two flip-flops which are set in succession by the output signals of said coincidence circuits upon attainment of the range limits respectively set by the associated limit setting unit;

a means for sampling the states of said flip-flops after termination of a preselected evaluation time span for generating said signal to one of said status memories;

and a means for inhibiting the outputs of said flip-flops such that either an inverse signal of a first of said flip-flops in a non-set state or the output of another of said flip-flops associated with a highest range limit which is attained is employed as said signal to one of said status memories.

6. The device of claim 5 wherein each limit setting unit further includes a plurality of NAND gates each having one input connected to a respective output of the counting stages of said binary counter through an inverter, and each NAND gate having a second input normally connected to a fixed potential representing a logic high signal and selectively connectable via a switch to a logic low level whereby the range of counter readings associated with a limit setting unit is determined by closing said switches for the second inputs of selected ones of said NAND gates.

7. The device of claim 5 wherein the number of flip-flops is three, each flip-flop having a Q output and a $\overline{Q}$ output, and wherein the number of said status memories is four, said status memories each having an input and said status memory inputs being respectively connected to first, second, third and fourth NAND gates, and wherein said means for inhibiting the outputs of said flip-flops are first and second AND gates, said first AND gate having inputs respectively connected to the Q output of a first of said flip-flops and the $\overline{Q}$ output of a second of said flip-flops, said second AND gate having inputs respectively connected to the Q output of said second flip-flop and the $\overline{Q}$ output of a third of said flip-flops, said first NAND gate having a first input connected to the $\overline{Q}$ output of said first flip-flop, said second NAND gate having a first input connected to the output of said first AND gate, said third NAND gate having a first input connected to the output of said second AND gate, and said fourth NAND gate having a first input connected to the Q output of said third flip-flop, each of said NAND gates having a second input connected to a means for generating a sampling pulse for periodically enabling said NAND gates for supplying a signal to one of said status memories.

* * * * *